United States Patent
Constantine et al.

(10) Patent No.: US 10,525,000 B2
(45) Date of Patent: Jan. 7, 2020

(54) COMPOSITION

(71) Applicant: COSMETIC WARRIORS LIMITED, Poole, Dorset (GB)

(72) Inventors: Mark Constantine, Poole (GB); Margaret Joan Constantine, Poole (GB); Helen Elizabeth Ambrosen, Wimborne (GB); Rowena Jacqueline Bird, Christchurch (GB)

(73) Assignee: COSMETIC WARRIORS LIMITED, Poole, Dorset (GB)

( * ) Notice: Subject to any disclaimer, the term of this patent is extended or adjusted under 35 U.S.C. 154(b) by 12 days.

(21) Appl. No.: 15/568,444

(22) PCT Filed: Apr. 21, 2016

(86) PCT No.: PCT/GB2016/051103
§ 371 (c)(1),
(2) Date: Oct. 20, 2017

(87) PCT Pub. No.: WO2016/170337
PCT Pub. Date: Oct. 27, 2016

(65) Prior Publication Data
US 2018/0104171 A1    Apr. 19, 2018

(30) Foreign Application Priority Data

Apr. 22, 2015 (GB) .................... 1506826.5

(51) Int. Cl.
| A61K 8/73 | (2006.01) |
|---|---|
| A61K 8/02 | (2006.01) |
| A61K 8/26 | (2006.01) |
| A61K 8/97 | (2017.01) |
| A61K 8/9789 | (2017.01) |
| A61K 8/19 | (2006.01) |

(52) U.S. Cl.
CPC ............ *A61K 8/732* (2013.01); *A61K 8/0216* (2013.01); *A61K 8/0241* (2013.01); *A61K 8/19* (2013.01); *A61K 8/26* (2013.01); *A61K 8/97* (2013.01); *A61K 8/9789* (2017.08); *A61K 2800/412* (2013.01); *A61K 2800/43* (2013.01); *A61K 2800/432* (2013.01); *A61K 2800/52* (2013.01)

(58) Field of Classification Search
None
See application file for complete search history.

(56) References Cited

U.S. PATENT DOCUMENTS

| 5,352,441 A | * | 10/1994 | Mausner | .................. A61K 8/11 424/490 |
|---|---|---|---|---|
| 2009/0142382 A1 | | 6/2009 | Shah et al. | |
| 2009/0304609 A1 | * | 12/2009 | Allemand | ................ A61K 8/02 424/59 |
| 2010/0183535 A1 | | 7/2010 | Goetz et al. | |
| 2012/0039831 A1 | | 2/2012 | Musumeci | |
| 2012/0177586 A1 | * | 7/2012 | Mehta | .................. A61K 31/047 424/59 |
| 2013/0236405 A1 | | 9/2013 | De Luigi | |

FOREIGN PATENT DOCUMENTS

| DE | 20308748 U1 | 8/2003 |
|---|---|---|
| DE | 102005051869 A1 | 4/2007 |
| GB | 2502339 A | 11/2013 |
| JP | 2006-282583 A | 10/2006 |
| KR | 20150021372 A | 3/2015 |
| WO | 2006/096506 A1 | 9/2006 |
| WO | 2010/070595 | 6/2010 |

OTHER PUBLICATIONS

Echkart, "Preliminary Technical Data Sheet SYNAFIL S 115", EE-35688 (2013).
International Search Report and Written Opinion for PCT/GB2016/051103, dated Jun. 22, 2016.
Search Report for British Patent Application No. 1506826.5, dated Jan. 28, 2016.
Mintel "Rouge Blush Pot", Database GNPD [online], XP002758368.
Mintel "Sateen Eye Colour", Database GNPD [online], XP002758369.
UK Examination Report under Section 18(3) issued in Patent Application No. GB1506826.5, dated Jun. 12, 2019.

* cited by examiner

*Primary Examiner* — David J Blanchard
*Assistant Examiner* — Sarah J Chickos
(74) *Attorney, Agent, or Firm* — Merchant & Gould P.C.

(57) ABSTRACT

A solid cosmetic composition includes (i) a natural colourant, (ii) starch, and (iii) mica.

18 Claims, No Drawings

COMPOSITION

This application is a National Stage of PCT/GB2016/051103, filed 21 Apr. 2016, which claims benefit of British Patent Application No. 1506826.5, filed 22 Apr. 2015 which applications are incorporated herein by reference. To the extent appropriate, a claim of priority is made to each of the above disclosed applications.

FIELD OF THE INVENTION

The present invention relates to a product for use as a cosmetic, a process for improving colour stability of a natural colourant, and a cosmetic method for using the cosmetic product.

BACKGROUND TO THE INVENTION

Ever since the Predynastic period, naturally occurring elements have been used as a way of accentuating certain bodily facets, such as the eyes and lips. Around 4000 BC, Ancient Egyptians applied galena mesdemet (a combination of copper and lead ore) and malachite (a combination of copper minerals) to their faces to enhance their natural features, act as a primitive insect repellent and prevent disease.

To this day natural elements have been used to decorate, enhance and emphasise the body and face to the point that colour cosmetics are a modern day staple. Nonetheless, natural elements—which throughout history have been used as colour cosmetics—have been overtaken by modern technology and scientific discovery. Research and development in the colour cosmetic industry has led to a dramatic improvement in the lightfastness, colour range and intensity of decorative cosmetic products, resulting in a global industry that is worth over $55 billion.

However, whilst this rapid expansion in the colour cosmetics market has undoubtedly proven popular with consumers, there is a general concern about the ingredients and trace elements present in cosmetic products. The cosmetic industry has been under particular scrutiny with regards to the dyes and colourants that are used in cosmetic products, particularly as it has been shown that dyes derived from coal tar and colourants containing azo-compounds are potentially toxic and mutagenic.

Consumers are increasingly more interested in the potential health benefits of the cosmetic products they use, resulting in the growing demand for natural and organic cosmetic compositions. Whilst natural cosmetic products may be free from harmful chemicals, preservatives and other additives, they often possess undesirable characteristics such as reduced lightfastness, colour stability, shelf life and ease of which they can be applied to the skin.

Colour cosmetic compositions are often formulated as oil or cream dispersions, which absorb into the skin and provide an even tone and finish. Unfortunately, these cosmetic compositions contain unfavourable and undesirable ingredients, such as pentylene glycol, dimethicone, silica and preservatives which can potentially cause irritation and damage to a user's skin, especially to sensitive areas around the user's eyes and face. Therefore, it is desirable to formulate cosmetic compositions without preservatives and other potentially harmful ingredients.

The present invention seeks to provide a solid cosmetic composition that addresses the problems of the prior art and does not contain preservatives and significantly harmful ingredients at a significant concentration, if at all.

SUMMARY OF THE INVENTION

In a first aspect there is provided a solid cosmetic composition comprising
(i) a natural colourant;
(ii) starch; and
(iii) mica.

In a second aspect there is provided a process for improving colour stability of a natural colourant, the process comprising the steps of
(i) providing a natural colourant;
(ii) mixing the natural colourant with starch and mica.

In a third aspect there is provided the use of starch and mica for improving colour stability of a natural colourant.

In a fourth aspect there is provided a method comprising contacting the skin of a user with the present product.

We found that by providing a combination of natural colourants with starch and mica, an exceptionally stable cosmetic composition is formed. This powdered composition is found to have superior colour stability in comparison to the natural colourant alone and in comparison to an analogous competitor product. The composition was also found to have a comparable colour stability to a synthetic colour cosmetic composition. The excellent colour stability of the present products has a number of advantages. For example, the user does not have to reapply the product since the colour is durable and will persist for a long period of time. It is also desirable from a retail perspective as the colour of the products will not fade upon an extended period of time on a shelf.

The present system allows for an anhydrous environment which may be devoid of preservatives and that does not require any additives to improve the flowability and ease of which the composition is applied to the user's skin.

An additional advantage of the present invention is that it can be incorporated into product packaging, as a dye, to indicate the colour, shade and hue of the individual cosmetic compositions, without fading over time. This is advantageous as it provides a true reflection of the cosmetic composition that is provided within the packaging.

For ease of reference, these and further aspects of the present invention are now discussed under appropriate section headings. However, the teachings under each section are not necessarily limited to each particular section.

DETAILED DESCRIPTION

Composition

As discussed herein, in one aspect of the present invention, there is provided a solid cosmetic composition comprising
(i) a natural colourant;
(ii) starch; and
(iii) mica.

As discussed herein, the cosmetic composition is a solid. Solid products of the present invention may be compositions which can substantially sustain their physical shape when unsupported by external means, e.g. packaging etc. Thus, they are considered to be solid, solid-like, in solid form or in solid-like form at room temperature. For the avoidance of doubt the solid product must remain substantially solid at up to 30° C.

By solid-like, it is understood that some materials are considered to be solid, yet over an extremely long period of time, may alter in shape, e.g. amorphous materials such as glass etc. However, they are considered to be solid-like as, for the purpose they fulfil, they are solid.

Due to the solid form of the compositions of the present invention, external packaging may not be required to maintain the shape of the composition.

Preferably the cosmetic composition is a powdered solid. By powdered solid, the skilled person understands that the cosmetic composition is a dry, bulk solid composed of a large number of very fine particles that may flow freely when shaken. Each particle is a solid particle or solid-like particle, where solid and solid-like are as defined above.

The solid cosmetic composition of the present invention may be used in any manner in which the end user sees fit. However, in a preferred aspect the solid cosmetic composition of the present invention is applied to the skin of a user in order to enhance their natural features.

Natural Colourant

As discussed herein, the solid cosmetic composition of the present invention contains a natural colourant. The natural colourant may be present in any suitable amount to provide the necessary properties of the final product. In one aspect the natural colourant is present in an amount of from 1 to 70% by weight of the solid cosmetic composition. In one aspect the natural colourant is present in an amount of from 1 to 67% by weight of the solid cosmetic composition. In one aspect the natural colourant is present in an amount of from 1 to 60% by weight of the solid cosmetic composition. In one aspect the natural colourant is present in an amount of from 1 to 55% by weight of the solid cosmetic composition. In one aspect the natural colourant is present in an amount of from 1 to 50% by weight of the solid cosmetic composition. In one aspect the natural colourant is present in an amount of from 1 to 45% by weight of the solid cosmetic composition. In one aspect the natural colourant is present in an amount of from 1 to 40% by weight of the solid cosmetic composition. In one aspect the natural colourant is present in an amount of from 1 to 35% by weight of the solid cosmetic composition. In one aspect the natural colourant is present in an amount of from 1 to 30% by weight of the solid cosmetic composition. In one aspect the natural colourant is present in an amount of from 1 to 25% by weight of the solid cosmetic composition. In one aspect the natural colourant is present in an amount of from 1 to 20% by weight of the solid cosmetic composition. In one aspect the natural colourant is present in an amount of from 1 to 15% by weight of the solid cosmetic composition. In one aspect the natural colourant is present in an amount of from 1 to 12% by weight of the solid cosmetic composition.

In one aspect the natural colourant is present in an amount of from 2 to 67% by weight of the solid cosmetic composition. In one aspect the natural colourant is present in an amount of from 3 to 60% by weight of the solid cosmetic composition. In one aspect the natural colourant is present in an amount of from 4 to 55% by weight of the solid cosmetic composition. In one aspect the natural colourant is present in an amount of from 5 to 50% by weight of the solid cosmetic composition. In one aspect the natural colourant is present in an amount of from 5 to 45% by weight of the solid cosmetic composition. In one aspect the natural colourant is present in an amount of from 5 to 40% by weight of the solid cosmetic composition. In one aspect the natural colourant is present in an amount of from 5 to 35% by weight of the solid cosmetic composition. In one aspect the natural colourant is present in an amount of from 5 to 30% by weight of the solid cosmetic composition. In one aspect the natural colourant is present in an amount of from 5 to 25% by weight of the solid cosmetic composition. In a preferred aspect the natural colourant is present in an amount of from 5 to 20% by weight of the solid cosmetic composition. In a preferred aspect the natural colourant is present in an amount of from 5 to 15% by weight of the solid cosmetic composition. In a preferred aspect the natural colourant is present in an amount of from 5 to 12% by weight of the solid cosmetic composition.

In a preferred aspect the natural colourant is present in an amount of from 1 to 25% by weight of the solid cosmetic composition. In a preferred aspect the natural colourant is present in an amount of from 2 to 25% by weight of the solid cosmetic composition.

Natural colourants are known to those skilled in the art and are materials and compositions which are naturally occurring and have the ability to colour compositions. In one aspect, the natural colourant is a colourant derived from organic sources. In one aspect, the natural colourant is a colourant not derived from inorganic sources. In one aspect, the natural colourant is a colourant derived from organic, and not inorganic, sources. In one aspect, the natural colourant is an organic pigment. The terms organic and inorganic are understood by those skilled in the art. Typically, an organic material is considered to be a material containing carbon. An inorganic material is one that is not organic.

In one aspect, the natural colourant is a colourant that is derived from plant-based material. In one aspect, the natural colourant is a colourant that a component of a plant. In one aspect the natural colourant is selected from beetroot, chlorophyll, gardenia, blackberry, coffee, rose, caramel powder, grape, alfalfa, walnut hull, calendula, cocoa, green tea, hibiscus, kelp, olive, orange, parsley, pumpkin, spinach, spirulina, wheatgrass sources, turmeric, butterfly pea, carrot, tomato and mixtures thereof.

In one aspect the natural colourant is selected from chlorophyll, carotenoids, anthocyanins, betalains and mixtures thereof.

Starch

As discussed herein, the present invention contains starch. The starch may be present in any suitable amount to achieve the desired properties of the solid cosmetic composition. In one aspect the starch is present in an amount of from 1 to 40% by weight of the solid cosmetic composition. In one aspect the starch is present in an amount of from 1 to 35% by weight of the solid cosmetic composition. In one aspect the starch is present in an amount of from 1 to 30% by weight of the solid cosmetic composition. In one aspect the starch is present in an amount of from 1 to 25% by weight of the solid cosmetic composition. In one aspect the starch is present in an amount of from 1 to 20% by weight of the solid cosmetic composition. In one aspect the starch is present in an amount of from 1 to 18% by weight of the solid cosmetic composition. In one aspect the starch is present in an amount of from 5 to 40% by weight of the solid cosmetic composition. In one aspect the starch is present in an amount of from 5 to 35% by weight of the solid cosmetic composition. In one aspect the starch is present in an amount of from 5 to 30% by weight of the solid cosmetic composition. In one aspect the starch is present in an amount of from 5 to 25% by weight of the solid cosmetic composition. In one aspect the starch is present in an amount of from 5 to 20% by weight of the solid cosmetic composition. In one aspect the starch is present in an amount of from 5 to 18% by weight of the solid cosmetic composition.

In one aspect the starch is present in an amount of from 2 to 40% by weight of the solid cosmetic composition. In one aspect the starch is present in an amount of from 2 to 35% by weight of the solid cosmetic composition. In one aspect the starch is present in an amount of from 2 to 30% by weight of the solid cosmetic composition. In one aspect the starch is present in an amount of from 2 to 25% by weight of the solid cosmetic composition. In one aspect the starch is present in an amount of from 2 to 20% by weight of the solid cosmetic composition. In one aspect the starch is present in an amount of from 3 to 20% by weight of the solid cosmetic composition. In one aspect the starch is present in an amount of from 4 to 20% by weight of the solid cosmetic composition. In one aspect the starch is present in an amount of from 4 to 15% by weight of the solid cosmetic composition. In one aspect the starch is present in an amount of from 4 to 10% by weight of the solid cosmetic composition. In one aspect the starch is present in an amount of from 5 to 10% by weight of the solid cosmetic composition.

The starch may be any suitable starch to provide the desired properties of the solid cosmetic composition. Preferably, the starch is selected from tapioca starch, corn starch, potato starch and mixtures thereof. Preferably the starch is tapioca starch.

In a preferred aspect there is provided a solid cosmetic composition comprising
 (i) a natural colourant;
 (ii) tapioca starch; and
 (iii) mica.

In a preferred aspect the starch is tapioca starch present in an amount of from 1 to 35% by weight of the solid cosmetic composition. Preferably the starch is tapioca starch present in an amount of from 4 to 10% by weight of the solid cosmetic composition.

Powdered colour cosmetic compositions are typically formulated to confer excellent slip, even coverage and optimal adhesion to the user's skin during application and use. It was surprisingly found by the present inventors that, in embodiments wherein the solid cosmetic composition is in powdered form, the use of tapioca starch produced excellent slip, coverage and adhesion characteristics. Slip agents are typically described as components that aid the application and maintain even coverage of the colour cosmetic composition over a prolonged period of time on the skin.

It was further found that the use of tapioca starch may provide excellent durability on the user's skin during use, and resulted in the solid cosmetic composition maintaining a smooth, even coverage for a prolonged period of time. Without wishing to be bound, it is thought that the excellent durability of tapioca starch is due to its reduced susceptibility to hydrolysis by transepidermal water loss and absorption of sebum and other oil-based secretions.

Mica

As discussed herein, the solid cosmetic composition of the present invention contains mica. The skilled person understands that the term mica refers to silicate minerals, which are a type of phyllosilicate exhibiting a two-dimensional sheet or layer structure. The general formula for minerals of the mica group is $XY_{2-3}Z_4O_{10}(OH, F)_2$, where X is K, Na, Ba, Ca, Cs, Rb, $H_3O$, or $NH_4$; Y is Al, Mg, $Fe^{2+}$, Li, Cr, Mn, V, or Zn; and Z is Si, Al, $Fe^{3+}$, Be, or Ti.

The mica may be present in any amount to provide the necessary properties of the final product. In one aspect the mica is present in an amount of from 20 to 95% by weight of the solid cosmetic composition. In one aspect the mica is present in an amount of from 25 to 95% by weight of the solid cosmetic composition. In one aspect the mica is present in an amount of from 30 to 95% by weight of the solid cosmetic composition. In one aspect the mica is present in an amount of from 35 to 95% by weight of the solid cosmetic composition. In one aspect the mica is present in an amount of from 40 to 95% by weight of the solid cosmetic composition. In one aspect the mica is present in an amount of from 45 to 95% by weight of the solid cosmetic composition. In one aspect the mica is present in an amount of from 50 to 95% by weight of the solid cosmetic composition. In one aspect the mica is present in an amount of from 40 to 90% by weight of the solid cosmetic composition. In one aspect the mica is present in an amount of from 50 to 90% by weight of the solid cosmetic composition. In one aspect the mica is present in an amount of from 55 to 85% by weight of the solid cosmetic composition. In one aspect the mica is present in an amount of from 60 to 80% by weight of the solid cosmetic composition. In one aspect the mica is present in an amount of from 65 to 75% by weight of the solid cosmetic composition.

In one aspect the mica is present in an amount of from 28 to 95% by weight of the solid cosmetic composition. In one aspect the mica is present in an amount of from 30 to 94% by weight of the solid cosmetic composition. In one aspect the mica is present in an amount of from 40 to 94% by weight of the solid cosmetic composition. In one aspect the mica is present in an amount of from 45 to 93% by weight of the solid cosmetic composition. In one aspect the mica is present in an amount of from 50 to 92% by weight of the solid cosmetic composition. In one aspect the mica is present in an amount of from 50 to 91% by weight of the solid cosmetic composition. In one aspect the mica is present in an amount of from 40 to 90% by weight of the solid cosmetic composition.

In a preferred aspect the mica is present in an amount of from 28 to 95% by weight of the solid cosmetic composition. In a preferred aspect the mica is present in an amount of from 40 to 94% of the solid cosmetic composition. In a preferred aspect the mica is present in an amount of from 50 to 95% by weight of the solid cosmetic composition.

In a preferred aspect the mica is synthetic mica. Preferably the synthetic mica is present in an amount of from 28 to 95% by weight of the solid cosmetic composition, such as in an amount of from 50 to 95% by weight of the solid cosmetic composition.

Therefore, in a preferred aspect there is provided a solid cosmetic composition comprising
 (i) a natural colourant;
 (ii) starch; and
 (iii) synthetic mica.

In one aspect the mica, and preferably synthetic mica, has a particle size range of 1 to 50 µm. In one aspect the mica, and preferably synthetic mica, has a particle size range of 2 to 50 µm. In one aspect the mica, and preferably synthetic mica, has a particle size range of 3 to 50 µm. In one aspect the mica has a particle size range of 4 to 50 µm. In one aspect the mica has a particle size range of 5 to 50 µm. In one aspect the mica has a particle size range of 10 to 50 µm. In one aspect the mica has a particle size range of 15 to 50 µm. In one aspect the mica, and preferably synthetic mica, has a particle size range of 1 to 15 µm. In one aspect the mica, and preferably synthetic mica, has a particle size range of 2 to 15 µm. In one aspect the mica, and preferably synthetic mica, has a particle size range of 3 to 15 µm. In one aspect the mica has a particle size range of 4 to 15 µm. In one aspect the mica has a particle size range of 5 to 15 µm.

In one aspect the mica is a mixture of one or more micas. In one aspect the mica is a mixture of one or more synthetic micas.

In a preferred aspect the mica comprises coloured mica. In a preferred aspect the mica comprises uncoloured mica. In a preferred aspect the mica is a mixture of uncoloured and coloured mica.

Preferably the mica is a mixture of uncoloured and coloured mica in a weight ratio of 10:90 to 50:50, such as in a weight ratio of 14:86 to 50:50, such as in a weight ratio of 15:85 to 50:50, such as in a weight ratio of 20:80 to 45:55, such as in a weight ratio of 30:70 to 40:60.

In one aspect the solid cosmetic composition comprises uncoloured mica in an amount of 10 to 50 wt. % and coloured mica in an amount of 50 to 90 wt. % based on the total content of mica. In one aspect the solid cosmetic composition comprises uncoloured mica in an amount of 14 to 50 wt. % and coloured mica in an amount of 50 to 86 wt. % based on the total content of mica. In one aspect the solid cosmetic composition comprises uncoloured mica in an amount of 20 to 45 wt. % and coloured mica in an amount of 55 to 80 wt. % based on the total content of mica. In one aspect the solid cosmetic composition comprises uncoloured mica in an amount of 30 to 40 wt. % and coloured mica in an amount of 60 to 70 wt. % based on the total content of mica.

In one preferred aspect the mica is a type of synthetic fluorphlogopite. Synthetic fluorphlogopite is known to be a synthetic mimic of a natural mineral that functions in cosmetics as a bulking agent and a viscosity increasing agent in aqueous solutions. Synthetic fluorphlogopite is partially composed of magnesium aluminium silicate sheets weakly bound together with potassium. The chemical formula of synthetic fluorphlogopite is $Mg_3KAlF_2O(SIO_3)_3$.

Natural Colourant, Starch and Mica

As discussed herein, in one aspect of the present invention, there is provided a solid cosmetic composition comprising
  (i) a natural colourant;
  (ii) starch; and
  (iii) mica.

In a preferred aspect of the present invention, there is provided a solid cosmetic composition comprising
  (i) a natural colourant in an amount of from 1 to 67% by weight of the solid cosmetic composition;
  (ii) starch in an amount of from 1 to 35% by weight of the solid cosmetic composition; and
  (iii) mica in an amount of from 28 to 95% by weight of the solid cosmetic composition.

In a preferred aspect of the present invention, there is provided a solid cosmetic composition comprising
  (i) a natural colourant in an amount of from 1 to 25% by weight of the solid cosmetic composition;
  (ii) starch in an amount of from 4 to 10% by weight of the solid cosmetic composition; and
  (iii) mica in an amount of from 50 to 95% by weight of the solid cosmetic composition.

In one aspect of the present invention, there is provided a solid cosmetic composition consisting essentially of
  (i) a natural colourant;
  (ii) starch; and
  (iii) mica.

In one aspect of the present invention, there is provided a solid cosmetic composition consisting of
  (i) a natural colourant;
  (ii) starch; and
  (iii) mica.

The term "consisting essentially of" is understood to mean that the cosmetic composition includes each of components (i), (ii) and (iii), and may also include additional components in amounts such that any additional components do not materially affect the basic and novel properties of the present invention. The term "consisting of" is understood to mean that the cosmetic composition includes each of components (i), (ii) and (iii), and includes no additional components.

The combined amount of the natural colourant, starch and mica in any amount to provide the desired physical characteristics of the solid cosmetic product. Preferably the combined amount of the natural colourant, starch and mica is from about 10% to about 100% by weight of the total composition. Preferably the combined amount of the natural colourant, starch and mica is from about 20% to about 100% by weight of the total composition. Preferably the combined amount of the natural colourant, starch and mica is from about 30% to about 100% by weight of the total composition. Preferably the combined amount of the natural colourant, starch and mica is from about 40% to about 100% by weight of the total composition. Preferably the combined amount of the natural colourant, starch and mica is from about 50% to about 100% by weight of the total composition. Preferably the combined amount of the natural colourant, starch and mica is from about 60% to about 100% by weight of the total composition. Preferably the combined amount of the natural colourant, starch and mica is from about 70% to about 100% by weight of the total composition. Preferably the combined amount of the natural colourant, starch and mica is from about 80% to about 100% by weight of the total composition. Preferably the combined amount of the natural colourant, starch and mica is from about 85% to about 100% by weight of the total composition. Preferably the combined amount of the natural colourant, starch and mica is from about 90% to about 100% by weight of the total composition. Preferably the combined amount of the natural colourant, starch and mica is from about 95% to about 100% by weight of the total composition. Preferably the combined amount of the natural colourant, starch and mica is 100% by weight of the total composition.

In one aspect of the present invention, there is provided a solid cosmetic composition comprising
  (i) a natural colourant;
  (ii) starch; and
  (iii) mica,
wherein the natural colourant is a colourant derived from organic, and not inorganic, sources.

In one aspect of the present invention, there is provided a solid cosmetic composition comprising
  (i) a natural colourant;
  (ii) starch; and
  (iii) mica,
wherein the natural colourant is a colourant derived from plant-based sources.

In one aspect of the present invention, there is provided a solid cosmetic composition comprising
  (i) a natural colourant;
  (ii) starch; and
  (iii) mica,
wherein the natural colourant is selected from beetroot, chlorophyll, gardenia, blackberry, coffee, rose, caramel powder, grape, alfalfa, walnut hull, calendula, cocoa, green tea, hibiscus, kelp, olive, orange, parsley, pumpkin, spinach, spirulina, wheatgrass sources, turmeric, butterfly pea, carrot, tomato and mixtures thereof.

In one aspect of the present invention, there is provided a solid cosmetic composition comprising
  (i) a natural colourant;

(ii) tapioca starch; and
(iii) mica,
wherein the natural colourant is a material and/or composition which is naturally occurring and which has the ability to colour compositions.

In one aspect of the present invention, there is provided a solid cosmetic composition comprising
(i) a natural colourant;
(ii) tapioca starch; and
(iii) mica,
wherein the natural colourant is a colourant derived from organic, and not inorganic, sources.

In one aspect of the present invention, there is provided a solid cosmetic composition comprising
(i) a natural colourant;
(ii) tapioca starch; and
(iii) mica,
wherein the natural colourant is a colourant derived from plant-based sources.

In one aspect of the present invention, there is provided a solid cosmetic composition comprising
(i) a natural colourant;
(ii) tapioca starch; and
(iii) mica,
wherein the natural colourant is selected from beetroot, chlorophyll, gardenia, blackberry, coffee, rose, caramel powder, grape, alfalfa, walnut hull, calendula, cocoa, green tea, hibiscus, kelp, olive, orange, parsley, pumpkin, spinach, spirulina, wheatgrass sources, turmeric, butterfly pea, carrot, tomato and mixtures thereof.

Additional Components

The solid cosmetic composition may contain one or more additional components such as to provide the desired composition. The person skilled in the art is aware of a range of cosmetically acceptable additives which are suitable for incorporation into such compositions. For examples, binders, fillers, opacifiers, perfumes, fragrances, decorative items and mixtures thereof.

As discussed herein, an advantage of the present invention is that synthetic colourants, such as dyes derived from coal tar and colourants containing azo-compounds, may be avoided. The presence of non-natural colourants is not excluded from the present composition. However, their absence is preferred. In one aspect the solid cosmetic composition may contain one or more additional colourants including one or more non-natural colourants. In one aspect the solid cosmetic composition is free of non-natural colourants.

In one aspect the solid cosmetic composition may contain one or more cosmetically acceptable bases such as one or more waxes or one or more vegetable butters.

In one preferred aspect the solid cosmetic composition comprises a humectant. Humectants, such as glycerine and vegetable oils, are well-known in the cosmetics industry for their ability to prevent transepidermal water loss, restoring normal skin barrier function, and acting as carriers of active ingredients.

In one preferred aspect, the solid cosmetic composition comprises a humectant selected from glycerine, vegetable oil and mixtures thereof. Preferably the vegetable oil is selected from the group consisting of sesame oil, rosehip oil, almond oil, raspberry seed oil, jojoba oil, avocado oil, castor oil, moringa oil, olive oil, grapeseed oil, argan oil, baobab oil, kalahari melon oil, brazil nut oil and mixtures thereof.

In one aspect the humectant is glycerine. In one aspect the humectant is a vegetable oil. In one preferred aspect the humectant is almond oil.

In one aspect the solid cosmetic composition comprises a humectant (preferably glycerine and/or a vegetable oil) in an amount of from 0.01 to 10% by weight of the total composition, such as in an amount of from 0.1 to 7.5% by weight of the total composition, such as in an amount of from 0.5 to 5% by weight of the total composition, such as in an amount of from 1 to 2.5% by weight of the total composition, such as in an amount of from 1 to 2% by weight of the total composition.

It was found by the present inventors that the addition of a humectant to solid cosmetic compositions of the present invention surprisingly altered the hue of the composition without adversely affecting the shelf-life of the composition. Therefore, it was found that the inclusion of a humectant in the solid cosmetic composition of the present invention may increase the range of colours that can be produced by natural colourants.

In addition, it was surprisingly found by the present inventors that, in embodiments wherein the solid cosmetic composition of the present invention is in the form of a powdered solid, the addition of glycerine and/or vegetable oil (preferably almond oil) to the composition modified the flowability of the powder such that a free- or easy-flowing powder may be produced, depending on the desired mode of application, such as by hand, brush, sponge or cotton bud. The application of the composition according to the present invention by hand or brush is better suited to powders with a higher flow factor value (i.e. which are more free-flowing), whereas application by sponge or cotton bud are better suited to powders with a lower flow factor value (i.e. are easy-flowing powders).

Therefore, in one preferred aspect of the present invention, there is provided a solid cosmetic composition comprising
(i) a natural colourant;
(ii) starch; and
(iii) mica,
wherein the solid cosmetic composition is a powdered solid composition, and wherein the solid cosmetic composition further comprises a humectant.

In one preferred aspect of the present invention, there is provided a solid cosmetic composition comprising
(i) a natural colourant;
(ii) starch; and
(iii) mica,
wherein the solid cosmetic composition is a powdered solid composition, and wherein the solid cosmetic composition further comprises a humectant selected from glycerine, vegetable oil, and mixtures thereof.

In one aspect the solid cosmetic composition contains one or more fragrances. Preferably the solid cosmetic composition comprises fragrance in an amount of no greater than 5% by weight of the solid cosmetic composition. If present, fragrance may be present in an amount of from 0.1 to 5% by weight of the total composition. The amount of fragrances is preferably from 0.1% to 5% by weight of the total composition, such as from 0.1% to 4% by weight of the total composition, such as from 0.5% to 5% by weight of the total composition, such as from 1% to 5% by weight of the total composition, such as from 0.5% to 4% by weight of the total composition, such as from 0.5% to 3% by weight of the total composition, such as from 0.5% to 2.5% by weight of the total composition, such as from 1.5% to 2.5% by weight of the total composition. Alternatively, in one aspect, the solid cosmetic composition is fragrance free.

The essential oils may be selected based on the fragrance desired, skin type to be treated and other effects desired based on the well-known properties of essential oils. The addition of essential oils, when taken in to the nose, is known to alter mood. For example, essential oils are known to create effects of drowsiness or stimulating the senses. Many effects can be achieved by the use of essential oils.

In one embodiment, the one or more essential oils present in the product are selected from Rosewood, Sandalwood, Chamomile, Eucalyptus, Tonka absolute, Lemon myrtle, Jasmin, Ylang ylang, Labdanum, Lemongrass, Rose Absolute, Grapefruit, Patchouli, Rosemary, Armois, Lemon, Neroli, Sweet violet, Lavender, Orange 50 fold, Vanilla, Peppermint, Benzoin, Hydrangia, Litsea Cubeba, Cardamon, Tonka, and Chamomile blue. In one embodiment, the one or more essential oils present in the product are selected from Rosewood, Sandalwood, Chamomile, Eucalyptus, Lavender, Tonka absolute, Rose absolute.

Vitamins, particularly B, C and E are very beneficial for the skin. Vitamin rich ingredients such as Wheatgerm oil can also be used to deliver vitamins on to the skin. In one embodiment, the vitamins are selected from vitamin B, vitamin C, vitamin E and mixtures thereof. It will be appreciated by one skilled in the art that the vitamin may be provided from any suitable source. For example the vitamin (s) may be provided from a synthetic source or from incorporation into the product of a material, such as a natural material, that has a high vitamin content.

The ingredients of the present invention do not require preservatives. The use of cosmetic preservatives can increase the potential to irritate the skin. In one aspect the solid cosmetic composition is free or substantially free of preservatives. Preferably the solid cosmetic composition comprises preservatives in an amount of no greater than 1% by weight of the solid cosmetic composition, such as in an amount of no greater than 0.5% by weight of the solid cosmetic composition, such as in an amount of no greater than 0.1% by weight of the solid cosmetic composition, such as in an amount of no greater than 0.01% by weight of the solid cosmetic composition, such as in an amount of no greater than 0.001% by weight of the solid cosmetic composition, such as in an amount of no greater than 0.0001% by weight of the solid cosmetic composition such as in an amount of 01% by weight of the solid cosmetic composition.

In one aspect the solid cosmetic composition contains water. In one aspect the solid cosmetic composition is free or substantially free of water. Preferably the solid cosmetic composition comprises water in an amount of no greater than 5% by weight of the solid cosmetic composition, such as in an amount of no greater than 4% by weight of the solid cosmetic composition, such as in an amount of no greater than 3% by weight of the solid cosmetic composition, such as in an amount of no greater than 2% by weight of the solid cosmetic composition, such as in an amount of no greater than 1% by weight of the solid cosmetic composition, such as in an amount of no greater than 0.5% by weight of the solid cosmetic composition, such as in an amount of no greater than 0.1% by weight of the solid cosmetic composition, such as in an amount of no greater than 0.01% by weight of the solid cosmetic composition.

The decorative items which may be present in the solid product include items such as glitter, paper such as rice paper, sequins, dried or fresh flowers, herbs, vegetables, parts thereof or mixtures thereof. Other enhancing materials may also be incorporated.

The above ranges provide preferred amounts of each of the components. Each of these ranges may be taken alone or in combination with one or more other component ranges to provide a preferred aspect of the invention.

Process

As discussed herein, the present invention provides a process for improving colour stability of a natural colourant, the process comprising the steps of
(i) providing a natural colourant;
(ii) mixing the natural colourant with starch and mica.

In one aspect the colour stability of the natural colourant is improved with respect to light. In a preferred aspect the colour stability of the natural colourant is improved with respect to UV light.

By "improving colour stability" it is meant that the colour of the natural colourant may persist for a longer period of time compared to the natural colourant alone. The skilled person understands this to mean that the colour of the natural colourant does not fade over an extended period of time when mixed with starch and mica in the process of the present invention. In one aspect the colour of the natural colourant may persist for a longer period of time when exposed to light compared to the natural colourant alone. In one aspect the colour of the natural colourant may persist for a longer period of time when exposed to UV light compared to the natural colourant alone.

Use

As discussed herein, the present invention provides a use of starch and mica for improving colour stability of a natural colourant. In one aspect the colour stability is improved with respect to light. In a preferred aspect the colour stability is improved with respect to UV light.

Method

In one aspect of the present invention, there is provided a method comprising contacting the skin of a user with the present product. The product may be self-applied by the user or applied by another individual.

In one aspect there is provided a method comprising directly contacting the skin of a user with the present product, wherein the present product is a solid cosmetic composition, preferably in powdered form.

In one aspect there is provided a method comprising first wetting the solid cosmetic product to form a paste, and immediately applying the resultant paste to the skin of a user. Preferably water is used to wet the solid cosmetic product. The use of water at all, and if used the amount of water required to wet the product prior to application onto a user's skin, is dependent upon the skin-type and physical outcome desired by the user. For example, if water is applied to the product a darker shade of colour may be provided. Therefore, for a single product a user may apply two shades of the colour based on whether water is or is not combined with the product. In any event, the amount of water used to wet the product prior to application should be minimal.

EXAMPLES

A general methodology for preparing compositions in accordance with the present invention is as follows:
1. Grind and homogenise the natural colourant, starch and a small fraction of the synthetic mica.
2. Sieve and screen the resulting powder to ensure a uniform particle size.
3. Thoroughly incorporate the remaining synthetic mica and press together.
4. Sieve and screen the final powdered composition to ensure a uniform particle size.

The invention will now be described with reference to the following non-limiting examples.

Example 1

A solid cosmetic composition of the present invention having the following composition was prepared

| Phase | Raw Material Type | Formula wt. % | Batch Size (g): 200 g |
|---|---|---|---|
| A | Tapioca Starch | 18.56 | 37.12 |
|   | Uncoloured mica | 17.51 | 35.02 |
|   | Cocoa powder | 12.15 | 24.30 |
| B | Coloured mica | 51.78 | 103.56 |
|   |   | 100.00 | 200.00 |

Method:
1. The tapioca starch was placed into a mixing vessel and slowly mixed with the cocoa powder.
2. After the tapioca starch and cocoa powder were fully blended together the mica was added and homogenised.
3. The resulting powder was sieved and screened after which the remaining synthetic mica was added whilst mixing.
4. The final powdered composition was ground to a uniform particle size, sieved and placed into suitable containers.

Example 2

A solid cosmetic composition of the present invention having the following composition was prepared.

| Phase | Raw Material Type | Formula wt. % | Batch Size (g): 200 g |
|---|---|---|---|
| A | Tapioca Starch | 9.95 | 19.90 |
|   | Uncoloured mica | 18.55 | 37.10 |
|   | Green Tea | 19.25 | 38.50 |
|   | Glycerine | 1.00 | 2.00 |
| B | Coloured mica | 51.25 | 102.50 |
|   |   | 100.00 | 200.00 |

Method:
1. The tapioca starch was placed into a mixing vessel and slowly mixed with the green tea and glycerine.
2. After the tapioca starch, green tea and glycerine were fully blended together the mica was added and homogenised.
3. The resulting powder was sieved and screened after which the remaining synthetic mica was added whilst mixing.
4. The final powdered composition was ground to a uniform particle size, sieved and placed into suitable containers.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. A solid cosmetic composition consisting of:
   (i) a natural colourant;
   (ii) starch; and
   (iii) mica.
2. A solid cosmetic composition according to claim 1 wherein the natural colourant is present in an amount of from 1 to 67% by weight of the solid cosmetic composition.
3. A solid cosmetic composition according to claim 1 wherein the natural colourant is present in an amount of from 1 to 25% by weight of the solid cosmetic composition.
4. A solid cosmetic composition according to claim 1, wherein the natural colourant is selected from beetroot, chlorophyll, gardenia, blackberry, coffee, rose, caramel powder, grape, alfalfa, walnut hull, calendula, cocoa, green tea, hibiscus, kelp, olive, orange, parsley, pumpkin, spinach, spirulina, wheatgrass sources, turmeric, butterfly pea, carrot, tomato and mixtures thereof.
5. A solid cosmetic composition according to claim 4 wherein the natural colourant is selected from chlorophyll, carotenoids, anthocyanins and betalains and mixtures thereof.
6. A solid cosmetic composition according to claim 1, wherein the starch is present in an amount of from 1 to 35% by weight of the solid cosmetic composition.
7. A solid cosmetic composition according to claim 1, wherein the starch is present in an amount of from 4 to 10% by weight of the solid cosmetic composition.
8. A solid cosmetic composition according to claim 1, wherein the starch is selected from tapioca starch, corn starch, potato starch and mixtures thereof.
9. A solid cosmetic composition according to claim 1, wherein the starch is tapioca starch.
10. A solid cosmetic composition according to claim 1, wherein the mica is synthetic mica.
11. A solid cosmetic composition according to claim 1, wherein the mica is present in an amount of from 28 to 95% by weight of the solid cosmetic composition.
12. A solid cosmetic composition according to claim 1, wherein the mica is present in an amount of from 50 to 95% by weight of the solid cosmetic composition.
13. A solid cosmetic composition according claim 1, wherein the mica has a particle size range of from 1 to 15 µm.
14. A solid cosmetic composition according to claim 1, wherein the mica is a mixture of micas.
15. A solid cosmetic composition according to claim 14 wherein the mica is a mixture of uncoloured mica and coloured mica.
16. A process for improving colour stability of a natural colourant the process consisting of the steps of:
   (i) providing a natural colourant,
   (ii) mixing the natural oolourant with starch and mica.
17. A process according to claim 16 wherein colour stability is improved with respect to light.
18. A process according to claim 16 wherein colour stability is improved with respect to UV light.

\* \* \* \* \*